United States Patent [19]

Mustich

[11] 4,103,025
[45] Jul. 25, 1978

[54] NOVEL TERPENES
[75] Inventor: Giuseppe Mustich, Milan, Italy
[73] Assignee: Inverni Della Beffa S.p.A., Milan, Italy
[21] Appl. No.: 778,458
[22] Filed: Mar. 17, 1977

Related U.S. Application Data
[63] Continuation of Ser. No. 541,588, Jan. 16, 1975, abandoned.

[30] Foreign Application Priority Data
Jan. 29, 1974 [GB] United Kingdom ............... 4042/74

[51] Int. Cl.² ................ A61K 31/215; A61K 31/22; C07C 69/74; C07C 69/78
[52] U.S. Cl. ............................. 424/305; 560/228; 260/410; 560/249; 560/256; 260/514.5; 424/308; 424/309; 424/310; 424/311; 424/312; 424/313; 424/314; 424/317; 424/318; 424/319; 560/6; 560/20; 560/37; 560/50; 560/51; 560/55; 560/72; 560/73; 560/75; 560/84; 560/105; 560/107; 560/156; 560/173; 560/174; 560/188; 560/192; 560/194; 560/219; 560/220
[58] Field of Search ............... 260/514.5, 468.5, 489, 260/488 B, 476 C, 410; 424/308, 311, 312, 317, 305, 309, 310, 313, 314, 318, 319; 560/6, 20, 37, 50, 51, 55, 72, 73, 75, 84, 105, 107, 156, 173, 174, 188, 192, 194, 219, 220, 228, 249, 256

[56] References Cited
PUBLICATIONS

Row et al., Tetrahedron Letters, No. 4, 129–134 (1962).
Row et al., Tetrahedron Letters, No. 27, pp. 12–16 (1960).
Row et al., Indian Journal of Chemistry, vol. 6, pp. 716–721 (1970).
Row et al., C.A, 63, p. 18178 (1965).
Bombardelli et al., cited in CA, 82, 98192e (1975).
Row et al., Tetrahedron, vol. 18, pp. 827–838 (1962).

Primary Examiner—Jane S. Myers
Attorney, Agent, or Firm—Browdy and Neimark

[57] ABSTRACT

Pharmaceutically active compounds of the formula

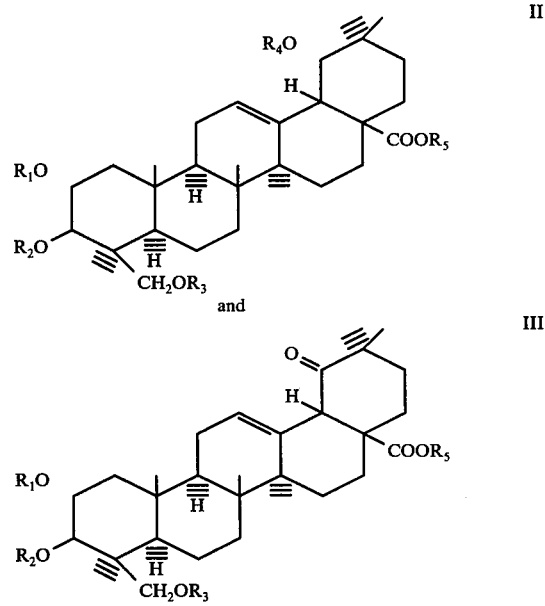

wherein —$OR_1$, —$OR_2$, —$OR_3$ and —$OR_4$, which may be the same or different, each represents a free or esterified hydroxyl group and —$COOR_5$ represents a free or esterified carboxyl group, are provided together with processes for their production and pharmaceutical compositions containing them. Compounds of formula II and III possess valuable cicatrizing and anti-inflammatory properties.

46 Claims, No Drawings

NOVEL TERPENES

This is a continuation of application Ser. No. 541,588, filed Jan. 16, 1975, now abandoned.

This invention relates to novel pharmaceutically active compounds, to processes for their production, to pharmaceutical compositions containing the compounds and to plant extracts from which the compounds may be prepared.

Plants of the genus Terminalia (of the family Combretaceae) are distributed over regions of Africa, Asia, Australia and tropical America. We have now discovered that extracts possessing valuable pharmaceutical properties may be obtained from plants of one particular species of this genus, namely *Terminalia sericea*.

These extracts have a high content of terpenic compounds and, in addition to the known compounds arjunic acid and arjunetine, they have been found to contain two hitherto unknown compounds which we have named sericic acid and sericoside. These compounds are respectively $2\alpha,3\beta,19\alpha,24$-tetrahydroxy-olean-12-en-28-oic acid and its D-glucopyranoside ester, and may be represented by the formula (I)

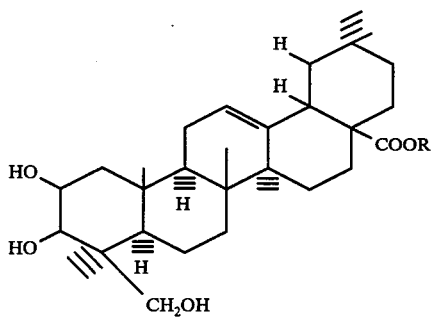

wherein in the case of sericic acid, R = hydrogen and in the case of sericoside, R = glucose.

Sericic acid and sericoside have been found to possess valuable cicatrigin, and anti-inflammatory properties which render them particularly useful in treating dermatological disorders, for example by being incorporated into cosmetics and in treating stomach ulcers. Sericic acid and sericoside may also be converted into derivatives which have similar valuable pharmacological properties.

Thus in accordance with one aspect of the present invention, there are provided compounds of the general formula (II) or (III)

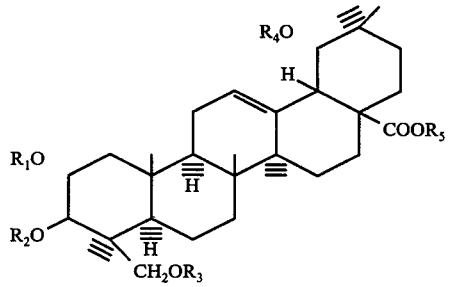

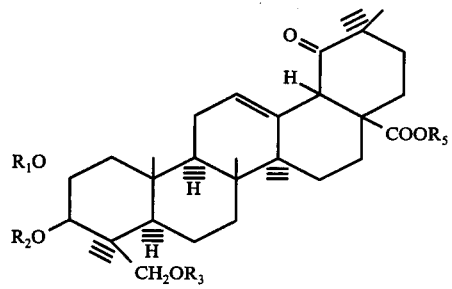

wherein $-OR_1$, $-OR_2$, $-OR_3$ and $-OR_4$ each represents a free or esterified hydroxyl group and $-COOR_5$ represents a free or esterified carboxyl group, and pharmaceutically acceptable salts of such compound which are capable of salt formation.

$R_1$, $R_2$, $R_3$ and $R_4$, which may be the same or different, may, for example, be substituted or unsubstituted aliphatic or aromatic mono- or poly-carboxylic acid acyl radicals, particularly such radicals containing up to twelve and preferably up to seven carbon atoms.

The aliphatic mono- or poly-carboxylic acid acyl radicals (both substituted and unsubstituted) may be straight or branched, chained or cyclic and furthermore may be saturated or unsaturated. Examples of saturated, unsubstituted aliphatic mono-carboxylic acid acyl radicals include acetyl, propionyl, butyryl, isobutyryl, valeryl, hexanoyl and heptanoyl. Particularly preferred are such radicals containing up to four carbon atoms.

Examples of poly-carboxylic acid acyl radicals include hemi-maleyl, hemi-fumaryl and hemi-succinyl.

Examples of aromatic carboxylic acid acyl radicals include benzoyl and phenylacetyl.

Where such radicals are substituted, the or each substituent may, for example, be selected from halogen (i.e. fluorine, chlorine, bromine or iodine), nitro, hydroxy, ether, keto and amino groups. The aromatic mono- or polycarboxylic acid acyl radicals may additionally or alternatively be substituted by one or more aliphatic radicals (optionally substituted, for example by one or more of the substituents referred to above) and preferably containing up to six carbon atoms as in methyl, ethyl, propyl, isopropyl, butyl, isobutyl, valeryl and hexyl.

Particularly preferred acryl radicals for $R_1$, $R_2$, $R_3$ and $R_4$ are acetyl, benzoyl and hemi-succinyl.

Where any one of $R_1$, $R_2$, $R_3$ and $R_4$ represents an acyl radical derived from a polycarboxylic acid, the remaining carboxyl (—COO—) group or groups may be in the form of the free acid (—COOH) or in the form of a derivative, for example an acid addition salt with a pharmaceutically acceptable cation or an ester with, for example, an aliphatic alcohol containing up to seven carbon atoms, such as, for example, methanol, ethanol, propanol, isopropanol, n-butanol, pentanol, hexanol and heptanol.

$R_5$ may, for example, be hydrogen or a substituted or unsubstituted straight, branched chain or cyclic aliphatic radical, particularly such radicals containing up to twelve and preferably up to seven carbon atoms. Examples of such radicals include methyl, ethyl, propyl, isopropyl, n-butyl, t-butyl, isobutyl, pentyl, cyclopentyl, hexyl, cyclohexyl and heptyl.

Where such radicals are substituted, the or each substitutent may, for example, be selected from halogen (i.e. fluorine, chlorine, bromine or iodine), nitro, hydroxy, ether, keto and amino groups. Any amino groups may be further substituted by one or two aliphatic radicals (which may be the same or different), for example the radicals specified above.

Particularly preferred examples of radicals represented by $R_5$ include hydrogen; the alkyl radicals referred to above; aminoalkyl radicals or mono- or dialkylminoalkyl radicals (—R'—NR"R"') where —R'— is a straight or branched chain alkylene radical, preferably containing up to seven carbon atoms (for example as in aminomethyl, 1,1- or 1,2-aminoethyl, aminopropyl, aminobutyl, aminopentyl, aminohexyl or aminoheptyl) and R" and R"', which may be the same or different are selected from hydrogen atoms and alkyl groups (for example the alkyl groups specified above); and glycosyl residues, particularly D-glucosyl.

Compounds of general formulae (II) and (III) containing carboxyl groups (for example where $R_5 = H$ or where $R_1$, $R_2$, $R_3$ or $R_4$ contains a free carboxyl group) may be converted to pharmaceutically acceptable acid addition salts, for example with metals yielding pharmaceutically acceptable cations, such as, for example, sodium, potassium, calcium, magnesium, aluminum or iron. Also, compounds containing substituted or unsubstituted amino groups may be converted to pharmaceuticaly acceptable acid addition salts with acids yielding pharmaceutically acceptable cations (e.g. hydrochloric or sulphuric acids).

The invention also includes pharmaceutical compositions comprising as active ingredient a compound of the general formula (II) or (III) or a pharmaceutically acceptable salt thereof in combination with a pharmaceutically acceptable excipient and processes for producing such compositions which comprise admixing the active ingredient with the excipient. Examples of excipients are starch, lactose, propylene glycol, triethanolamine, water and anti-fermentative agents.

According to a further aspect of the present invention there is provided a process for producing a compound of general formula (II) or (III) which comprises extracting tissue of a plant of the species *Terminalia sericea*, and in particular the roots or the bark of the roots with an organic solvent, isolating sericic acid and/or sericoside from the extract and if desired converting the isolated sericic acid or sericoside to another compound of general formula (II) or (III).

The organic solvent may, for example, be an alcohol (preferably a lower alcohol containing up to six carbon atoms and most preferably up to four carbon atoms, such as methanol, ethanol, n-propanol, isopropanol, or one of the butanols), a ketone (preferably a di-lower alkyl ketone wherein the lower alkyl groups contain up to six and preferably up to four carbon atoms as in acetone, methyl ethyl keton and di-isopropyl ketone) or an ester (preferably an ester formed with a lower alcohol containing up to six carbon atoms, and most preferably up to four carbon atoms, such as methanol, ethanol, n-propanol, isopropanol, the butanols and amyl alcohol and a lower alkanoic acid containing up to four carbon atoms, such as formic, acetic, propionic or butyric acids).

Particularly useful solvents are ethanol, acetone and ethyl acetate.

Where the organic solvent is miscible with water, mixtures of the solvent and water may be used.

Preferably, prior to isolating sericic acid and/or sericoside from the extract, fatty and resinous substances are removed, for example by evaporating the organic solvent from the extract and contacting the residue so obtained with a liquid hydrocarbon so as to form a partially purified extract. Preferably, the residue is diluted with water or with an alcohol/water mixture before it is contacted with the hydrocarbon. The fatty and resinous substances are preferentially dissolved in the hydrocarbon and may therefore be removed by deanting the resulting hydrocarbon solution.

Sericic acid has been found to be generally more soluble in chlorinated hydrocarbon solvents than in water and sericoside has been found to be generally more soluble in aqueous solvents than chlorinated hydrocarbons. The isolation of sericic acid and sericoside from the partially purified extract obtained as described above therefore preferably includes a fractionation step in which the extract is fractionated into a fraction containing sericic acid and other non-glucosidated terpenes (Fraction A) and a fraction containing sericoside and other terpenic glucosides by contacting a solution of the partially purified extract in water or a mixture of water and an alcohol (for example one of the alcohols specified above) with a chlorinated hydrocarbon solvent such as, for example, chloroform, methylene chloride or dichloroethane, and separating the aqueous and chlorinated hydrocarbon solutions so obtained.

The aqueous solution may then be diluted with alcohol to give an alcohol concentration of not less than 60% and treated to remove proteinaceous material by adding neutral or basic lead acetate solution and filtering to remove any precipitate which is formed. The filtrate may then be evaporated to form an aqueous concentrate by eliminating the alcoholic solvent and the terpenic glucosides extracted repeatedly from the concentrate with a mixture of butanol and benzene (preferably 3:1 to 4:1), The solution in the butanol/benzene mixture may then be evaporated to small volume and the residue poured into isopropyl ether. The precipitate so obtained contains a major part of the terpenic glucosides (Fraction B).

Sericic acid and sericoside may be obtained from Fractions A and B respectively by recrystallization or chromatographic separation.

It will be appreciated that the sericic acid- and sericoside-containing extracts of *Terminalia sericea* referred to above and in particular the purified fractions referred to as Fractions A and B constitute further aspects of the present invention.

Sericic acid and sericoside may each be transformed into each of the other compounds of general formulae (II) and (III) by known methods of esterification, hydrolysis, oxidation and salt formation and such methods form a further aspect of the present invention.

Thus, for example, sericic acid may be converted to sericoside by esterification with α-bromo-(tetra-acetyl)-glucose followed by successive elimination of the acetyl radicals and sericoside may be converted to sericic acid by saponification.

The following Examples illustrate the invention:

EXAMPLE 1

A - Separation of Fractions A and B 200 kg. of finely ground roots of plants of the species Terminalia sericea are extracted under weak reflux four times using 600 liters of aqueous alcohol each time. The reunited exracts are evaporated in vacuo to 100 liters and the aqueous residue extracted three times with ligroin using 100 liters of ligroin each time. The ligroin, which contains fatty acids, resins and β-sitosterol removed from the residue is decanted and the residue, in ethanol solution, is diluted with 300 liters of water and extracted three times with dichloroethane using 100 liters each time.

The dichloroethane solution so obtained is evaporated to dryness in vacuo and 2.5 kg. of residue are obtained containing sericic acid and other free triterpenes (Fraction A).

The aqueous residue remaining after the extraction with dichloroethane is diluted with 500 liters of alcohol and 10 kg. of neutral lead acetate dissolved in 30 liters of alcohol are added. An abundant precipitate is formed and is left to stand overnight to sediment. The precipitate is centrifuged and discarded, and the water-alcohol phase is concentrated in vacuo to about 200 liters. The aqueous concentrate is extracted three times with a mixture of t-butanol-benzene in the ratio 3:1 (v/v) using 100 liters each time.

The organic phase is separated and washed with a 10% solution of sodium carbonate and then evaporated in vacuo to 20 liters. The butanolic concentrate so obtained is poured, with vigorous agitation, into 150 liters of diethyl ether. A precipitate comprising triterpenic glucosides is formed and is centrifuged and dried. 5 kg. of product are obtained, containing sericoside and other triterpenic glucosides (Fraction B).

B - Preparation of purified sericic acid by crystallization 1 kg. of Fraction A is dissolved in 5 liters of alcohol. The solution is decolorized with carbon, evaporated to 3 liters and left to stand overnight.

300 g. of crude sericic acid crystallize, which by successive recrystallization from dilute aqueous alcohol or acetic acid enables 200 g. of pure sericic acid having m.p. 278° – 82° C, $[\alpha]_D^{30} = + 37.8$ (c = 0.32 EtOH 95) to be obtained.

Additional quantities of sericic acid may be obtained by reuniting the mother liquors, which are then evaporated to dryness, to obtain a residue which is acetylated in acetone, using acetic anhydride. 80 g. of sericic acid triacetate are obtained which after recrystallization from glacial acetic acid melts at 183° C and has $[\alpha]_D = +4°$ (c = 2, EtOH 95) IR 3630 cm$^{-1}$ 1745 cm$^{-1}$ and 1705 cm$^{-1}$.

By saponification with alcoholic potash the sericic acid triacetate may be converted to sericic acid, in a state of purity such that its properties are entirely identical with that obtained by crystallization, as described above.

C - Preparation of sericic acid by a chromotographic procedure 1 kg. of Fraction A is dissolved in 3 volumes of chloroform and chromatographed on a column containing 15 kg. of silica gel by eluting with a solvent mixture comprising 95:5 chloroform - ethanol. The fractions containing the individual pure components are collected and reunited and after crystallization from methanol, 250 g. of pure sericic acid having a m.p. 278° – 82° C are obtained along with 20 g. of arjunic acid with m.p. 220 ° – 22° C.

D - Preparation of sericoside by crystallization 1 kg. of Fraction B is dissolved in 6 liters of alcohol. The solution is decolorized with carbon and evaporated to 3 liters.

1 liter of hot water (at about 50° C) is added and the liquid is left to stand overnight. 600 g. of crude sericoside crystallize which, after repeated crystallizations from dilute alcohol, furnish 250 g. of pure sericoside having the following characteristics: m.p. 206° – 208° C and $[\alpha]_D = + 5.4$ (c = 2. pyridine).

E - Preparation of sericoside by chromatography 1 kg. of fraction B is dissolved in 3 liters of an 8:2 (v/v) chloroform - ethanol mixture and chromatographed on 30 kg. of silica gel by eluting with the said solvent mixture. The fractions containing the individual pure products are reunited and concentrated to dryness. After crystallization from methanol there are obtained respectively 320 g. of sericoside having an m.p. of 206 - 208° C and 210 g. of arjunetine.

EXAMPLE 2

Preparation of methyl sericate 10 g. of sericic acid are dissolved in 50 ml. of chloroform and treated with a solution of diazomethane in methylene chloride until complete reaction. The solution is concentrated in vacuo to dryness and the residue is crystallized from acetone.

EXAMPLE 3

Preparation of tribenzoyl methyl sericate 10 g. of methyl sericate are dissolved in 50 ml. of anhydrous pyridine and 9.24 g. of benzoyl chloride are added. The reaction mixture is left to stand for one night, then poured into water. Tribenzoyl methyl sericate precipitates, and after crystallization from methanol has a melting point of 199° C.

EXAMPLE 4

Preparation of triacetyl 19-keto methyl sericate 10 g. of methyl triacetylsericate (prepared in an analogous manner to methyl tribenzoyl sericate) are dissolved in 500 ml. of anhydrous acetone and Jones's reagent is added until the reaction is complete.

The acetone solution is diluted with 1,500 ml. of water whereupon the product precipitates in amorphous form.

The product is collected by filtration, and recrystallized from aqeuous methanol. After drying, there are obtained 9 g. of triacetyl 19-keto methyl sericate having an m.p. of 200 and $[\alpha]_D = + 33$ (c = 0.5, EtOH).

EXAMPLE 5

Preparation of diethylaminoethyl sericate 10 g. of potassium sericate are dissolved in 50 ml. of dimethyl formamide and treated with 3 g. of diethylaminoethyl chloride. The reaction mixture is kept at 50° C for 5 hours, then poured into 600 ml. of water. An abundant precipitate forms which is filtered, washed with water and recrystallized from aqueous isopropanol. The product melts at 105 ° – 8° C and $[\alpha]_D = +19.7°$ (c = 1, EtOH).

EXAMPLE 6

Table 1

| Treatment Substance | mg/kg | Number of animals | Number of ulcers of each class[2] | | | | | Ulcer Index | Percentage ulcer variation in relation to controls | Number of non-ulcerated stomachs (per cent) |
|---|---|---|---|---|---|---|---|---|---|---|
| | | | I | II | III | IV | V | | | |
| Controls (gum arabic 10%) | — | 13 | 338 (338) | 36 (180) | 10 (100) | 9 (180) | 9 (180) | 75 | — | — |
| Sericoside | 200 | 13 | 369 (369) | 15 (75) | 1 (10) | 0 (0) | 3 (60) | 39.5 | −48 | 7.6 |
| Sericic acid | 200 | 13 | 279 (279) | 12 (60) | 3 (30) | 2 (40) | 9 (180) | 45 | −45 | — |

[1]Doses administered orally 5 times, 42, 30, 25 and 6 hours prior to and immediately after the tying of the pylorus.
[2]In parentheses the product of the number of ulcers and the numerical value attributed to the individual classes according to the individual classes according to the evaluation criterion of T. O. Keyrilainen and M. K. Paasonen (Acta Pharmacol. et. Toxicol. 13, 22, 1957)

Preparation of methyl tetracetyl sericate 20 g. of methyl triacetylsericate are dissolved in 30 ml. of acetic anhydride and 1 ml. of concentrated perchloric acid is added. The reaction mixture is left to stand for 1 hour, then poured into 500 ml. of water.

There is precipitation of the product which, after filtration, is crystallized from ethanol.

The product melts at 223° C.

EXAMPLE 7

Preparation of methyl tetracetyl 18α-sericate 10 g. of methyl triacetyl sericate are dissolved in 50 ml. of 40% hydrobromic acid in acetic acid and left at room temperature for 30 hours. The reaction mixture is poured into water. The product is filtered and precipitates, and after drying it is crystallized from hexane. 6 g. of methyl tetracetyl 18α-sericate are obtained having an m.p. of 194° C and $[\alpha]_D = +12.6°$ (c = 0.4 in EtOH).

EXAMPLE 8

Preparation of 2,3,24-trihemisuccinyl derivative of sericic acid 10 g. of sericic acid are dissolved in 50 ml. of anhydrous pyridine and 10 g of succinic anhydride are added.

The reaction mixture is reheated to 80° C for 6 hours, then cooled and diluted with 800 ml. of chloroform.

The solution is counter-washed with 10% aqueous HCl until the pyridine is eliminated and then concentrated to dryness and dehydrated over $Na_2SO_4$.

The residue is crystallized from glacial acetic acid and 11 g. of trihemisuccinyl sericic acid with m.p. of 105° – 108° C and $[\alpha]_D = +2.65°$ (c = 2, EtOH) is obtained.

By following the general procedures of the above Examples 2 to 8, but using appropriate alternaive reactants other compounds of general formulae (II) or (III) may be prepared.

The following pharmaceutical data is given to illustrate the anti-inflammatory and cicatrizing properties of the compounds of the invention:

Anti-ulcer activity - Gastric Ulcer in the rats induced by Shay's method

The anti-ulcer activity of sericic acid and sericoside was determined by administering the compounds to rats in which gastric ulcers were induced by Shay's method. The compounds were administered at the dose of 200 mg./kg. orally five times, at 42, 30, 25 and 6 hours before tying of the pylorus and immediately after the operation and as shown in Table 1 diminished the ulcer index by 48 and 45 per cent respectively, compared with the controls.

LD 50 in Mice

The $LD_{50}$ in mice (as determined with intraperitoneal administration) for sericic acid and sericoside was as follows:

Sericic acid > 1,000 mg./kg.
Sericoside > 1,000 mg./kg.

Anti-inflammatory Activity Against Carragenin-induced Oedema in Rats

The anti-inflammatory activities of sericoside and sericic acid were determined by measuring the extent to which the oedema caused by sub-plantar administration of carragenin to rats could be inhibited by prior oral and intraperitoneal and administration of the substances.

The following were obtained:

1. Oral Administration

| Treatment | Doses mg/kg[1] | No. of animals | Volume of oedema in ml. (Average ±S.D)[2] | Percentage inhibition of the oedema |
|---|---|---|---|---|
| Controls | — | 10 | 0.30 ± 0.005 | — |
| Sericoside | 200 | 10 | *0.22 ± 0.010 | 26 |
| Sericic acid | 200 | 10 | *0.23 ± 0.009 | 23 |

*Significantly different (P < 0.05) from the average obtained with the controls according to Student's "t" test.
[1]Doses administered orally for 3 days; on the third day the administration was effected two hours before the subplantar injection of carragenin.
[2]Maximum volume of the oedema measured 3 hours after the subplantar injection of carragenin.

| Treatment | Doses mg/kg (1) | No. of animals | Volume of the oedema in ml. Average±S.D.) (2) | Percentage inhibition of the oedema |
|---|---|---|---|---|
| Controls | — | 10 | 0.31 ± 0.010 | — |
| Sericoside | 100 | 10 | 0.10 ±0 0.008 (*) | 67 |
| Sericic Acid | 100 | 10 | 0.11 ± 0.006 (*) | 64 |
| Controls | — | 10 | 0.31 ± 0.006 | — |
| Sericoside | 50 | 10 | 0.20 ± 0.005 (*) | 35 |
| Sericic acid | 50 | 10 | 0.23 ± 0.008 (*) | 25 |

(*) Significantly different (P<0.05) from the average obtained with the controls according to Student's "t" test.
(1) Administration endoperitoneally 30 minutes prior to the injection of carragenin.
(2) Maximum volume measured after 3 hours.

Cicatrizing Activity Upon Experimental Wounds in Rats

The cicatrizing activity of sericic acid and sericoside upon experimental wounds was determined on rats in accordance with the method of Morton & Malone (Arch. Int. Pharmacodyn. Ther. 196, 117, 1972).

The treatment of the wounds was effected with a 10% suspension of the active principles in water containing 2% carboxymethyl cellulose (CMC). The suspensions were used in doses of 0.1 ml. for each application, one treatment being effected per day.

From the data shown in the following Table 2 it can be seen that sericic acid and sericoside possess significant healing activity, compared with the controls, especially in the first days of treatment.

Table 2

Cicatrizing activity upon experimental wounds in the rat

| Treatment | ml./rat/day | No. of animals | Percentage remargination. Average ± S.D. | | | | |
|---|---|---|---|---|---|---|---|
| | | | Day I | Day II | Day III | Day V | Day VI |
| Control (2% CMC) | 0.1 | 14 | 5.2 ± 1.1 | 12.8 ± 1.5 | 21.9 ± 3.1 | 39.63 ± 2.3 | 57.4 ± 2.1 |
| Sericoside | 0.1 | 14 | 13.9 ± 1.4* | 23.7 ± 1.5* | 36.8 ± 2.0* | 53.30 ± 2.8* | 68.2 ± 2.1* |
| Sericic acid | 0.1 | 14 | 10.4 ± 1.3* | 23.7 ± 2.3* | 36.9 ± 2.7* | 48.00 ± 1.5* | 59.0 ± 2.2 |

Note: Topical treatment effected on each of the days on which measurements were taken (I, II, III, V, and VI).
*Significantly ($P<0.05$) different from the controls (2% CMC) based upon Student's "t" test.

Activity Against Ultra-Violet Ray Erythema

Ultra-violet ray erythema in guinea pigs was effected in accordance with the method of Winder et al. (Arch. Int. Pharmacodyn, 106, 261, 1968).

Sericoside and sericic acid were applied to the depilated skin of male albino guinea pigs (average weight 300 - 400 g) in the form of a 5% gel (using 200 mg. thereof) one hour prior to irradiation. The animals were depilated 18 hours prior to the irradiation and irradiated for 3 minutes with a 500 W. mercury vapor lamp at a distance of 18 cms.

The controls were treated with a similar gel which did not contain the active ingredients, sericoside or sericic acid.

The compounds under examination were able to reduce the erythema with a most pronounced activity at 8 hours, as shown by the results set forth in the following Table 3.

Table 3

UV Erythema in the Guinea Pig

| Treatment | Number of animals | Erythema Score** | | | | |
|---|---|---|---|---|---|---|
| | | 2 h. | 4 h. | 6 h. | 8 h. | 22 h. |
| Controls | 10 | 1.15 ± 0.17 | 2.40 ± 0.30 | 2.55 ± 0.34 | 2.35 ± 0.18 | 1.05 ± 0.23 |
| Sericoside | 10 | 0.75 ± 0.17 (34.8) | 1.70 ± 0.23 (29.2) | 1.95 ± 0.22 (23.5) | 1.30 ± 0.25* (44.7) | 0.70 ± 0.15 (33.3) |
| Sericic acid | 10 | 0.95 ± 0.12 (17.4) | 1.80 ± 0.21 (25) | 2.05 ± 0.22 (19.6) | 1.35 ± 0.18* (42.5) | 0.60 ± 0.10 (42.8) |

*Significantly ($P<0.05$) different from the controls, according to Duncan's test (analysis of the variation).
**0 = no erythema; 0.5 = moderate reddening; 1 = marked reddening; 2 = obvious erythema.
Note: The percentage inhibition compared with the controls is entered in parentheses.

Pharmaceutical Preparations

The following examples of pharmaceutical preparations were prepared by admixing the active ingredients with the excipients referred to and illustrate the manner in which the compounds of the invention may be brought into forms suitable for topical and oral administration.

| 1 % Gel for Topical Application | |
|---|---|
| 1) Sericoside | 1 g. |
| Excipients (propylene glycol, Carbopol 934, ethyl alcohol, triethanolamine, water, antifermentative) q.s. | 100 g. |
| 2) Sericic acid | 1 g. |
| Excipients (propylene glycol, Carbopol 934, ethyl alcohol, triethanolamine, water, antifermentative) q.s. | 100 g. |

| 1 % Ointment for Topical Application | |
|---|---|
| Sericoside | 1 g. |
| Excipients (glycerine, cetyl alcohol, saturated vegetable triglycerides, lanoline oil, propylene glycol, water) q.s. | 100 g. |

| Suspension for Oral Administration | |
|---|---|
| Sericic acid | 1 g. |
| Excipients (sodium alginate, corn starch, saccarose, water, antifermentative) q.s. | 100 g. |

| Powder for Topical Application | |
|---|---|
| 1) Sericoside | 2 g. |
| Excipients (Microlan, corn starch, magnesium stearate, talc) q.s. | 100 g. |
| 2) Sericic acid | 2 g. |
| Excipients (Microlan, corn starch, magnesium stearate, talc) q.s. | 100 g. |

| Ampoule for Injection | |
|---|---|
| 1) Sericic acid | 10 mg. |
| Excipients (propylene glycol, ethyl alcohol, sterile pyrogen free water) q.s. | 1 ml. |
| 2) Sericoside | 20 mg. |
| Excipients (propylene glycol, ethyl alcohol, sterile pyrogen-free water) q.s. | 2 ml. |

| Confections | |
|---|---|
| 1) Sericoside | 20 mg. |
| Excipients (corn starch, lactose, talc, magnesium stearate, sodium alginate, sugar, gum arabic, magnesium carbonate) q.s. | 250 mg. |
| 2) Sericic acid | 10 mg. |
| Excipients (corn starch, lactose, talc, magnesium stearate, sodium alginate, sugar, gum arabic, magnesium carbonate) q.s. | 200 mg. |

| Transparent gel | |
|---|---|
| Sericic acid | 10 g. |
| Excipients (propylene glycol, triethanolamine, water, | |

-continued

| Transparent gel | |
|---|---|
| antifermentative) q.s. to | 200 g. |

| Transparent gel | |
|---|---|
| Sericoside | 5 g. |
| Excipients (propylene glycol, triethanolamine, water, antifermentative) q.s. to | 200 g. |

| Tablets | |
|---|---|
| Sericoside | 100 mg. |
| Excipients (starch, lactose) q.s. to | 500 mg. |

I claim:

1. A derivative of sericic acid, having anti-inflammatory and cicatrizing properties, comprising a compound of the general formula

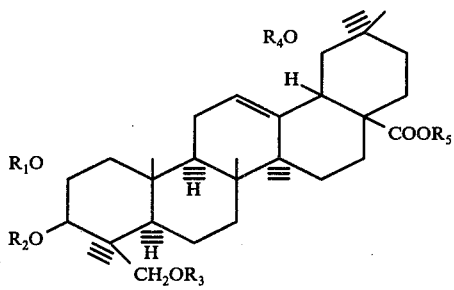

in which the hydrogen atom attached to $C_{18}$ is in the beta configuration, and in which $R_1$, $R_2$, $R_3$ and $R_4$ each represent a hydrogen atom or a substituted or unsubstituted aliphatic or aromatic mono- or polycarboxylic acid acyl radical, wherein when more than one of $R_1$, $R_2$, $R_3$ and $R_4$ are acyl radicals, they are the same acyl radical, and $R_5$ represents a hydrogen atom or a substituted or unsubstituted aliphatic radical, and in which $R_1$ to $R_5$ are not all hydrogen.

2. A compound in accordance with claim 1 wherein one or more of $R_1$, $R_2$, $R_3$ and $R_4$ is an unsubstituted acyl radical selected from the group consisting of acetyl, propionyl, butyryl, isobutyryl, valeryl, hexanoyl, heptanoyl, hemi-maleyl, hemi-fumaryl, hemi-succinyl, benzoyl and phenylacetyl.

3. A compound in accordance with claim 2 wherein said acyl radical is hemi-maleyl, hemi-fumaryl, or hemi-succinyl in which the remaining carboxyl group is in the form of the free acid, an acid addition salt with a pharmaceutically acceptable cation or an ester with an aliphatic alcohol containing up to seven carbon atoms.

4. A compound in accordance with claim 1 wherein one or more of $R_1$, $R_2$, $R_3$ and $R_4$ is a substituted acyl radical selected from the group consisting of acetyl, propionyl, butyryl, isobutyryl, valeryl, hexanoyl, heptanoyl, hemi-maleyl, hemi-fumaryl, hemi-succinyl, benzoyl and phenylacetyl, wherein said substituents are selected from the group consisting of halogen, nitro, hydroxy, ether, keto and amino groups.

5. A compound in accordance with claim 4 wherein said acyl radical is benzoyl or phenylacetyl, substituted by one or more substituents selected from the group consisting of halogen, nitro, hydroxy, ether, keto and amino groups and aliphatic radicals containing up to six carbon atoms, said aliphatic radicals being unsubstituted or substituted by one or more of halogen, nitro, hydroxy, ether, keto and amino groups.

6. A compound as claimed in claim 1 in which each of $R_1$, $R_2$, $R_3$ and $R_4$ represents hydrogen.

7. A compound as claimed in claim 1 in which each of $R_1$, $R_2$, $R_3$ and $R_4$ represents acetyl.

8. A compound as claimed in claim 1 in which each of $R_1$, $R_2$, $R_3$ and $R_4$ represents benzoyl.

9. A compound as claimed in claim 1 in which each of $R_1$, $R_2$, $R_3$ and $R_4$ represents hemisuccinyl.

10. A compound as claimed in claim 1 in which $R_5$ is an alkyl group.

11. A compound as claimed in claim 1 in which $R_5$ is an aminoalkyl or a mono- or dialkylaminoalkyl group.

12. A compound as claimed in claim 11 in which each of $R_1$, $R_2$, $R_3$ and $R_4$ represent hydrogen.

13. A compound as claimed in claim 1 in which $R_5$ is hydrogen.

14. A compound as claimed in claim 1 in which $R_5$ is methyl.

15. A compound as claimed in claim 1 in which $R_5$ is diethylaminoethyl.

16. A compound in accordance with claim 1 wherein $R_5$ is —R'—NR"R"', wherein R' is a straight or branched chain alkylene radical containing up to seven carbon atoms and R" and R"', which may be the same or different, are hydrogen atoms or a straight or branched chain alkylene radical containing up to seven carbon atoms.

17. A compound in accordance with claim 16 wherein $R_1$, $R_2$, $R_3$ and $R_4$ are all hydrogen.

18. Methyl sericate as claimed in claim 1.

19. Tribenzoyl methyl sericate as claimed in claim 1.

20. Diethylaminoethyl sericate as claimed in claim 1.

21. Methyl tetracetyl sericate as claimed in claim 1.

22. 2,3,24-Trihemisuccinyl sericic acid as claimed in claim 1.

23. A pharmaceutically acceptable salt of a compound according to claim 1 capable of salt formation.

24. Sericic acid, having the general formula

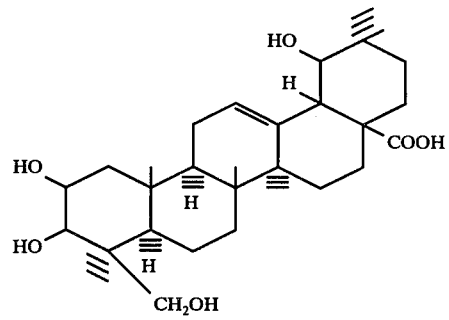

in pure form.

25. Sericic acid in accordance with claim 24 in crystalline form.

26. Methyl tetracetyl 18α-sericate.

27. A pharmaceutical composition consisting essentially of an anti-inflammatory amount of an active principle of the general formula

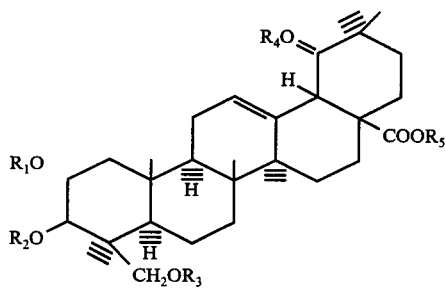
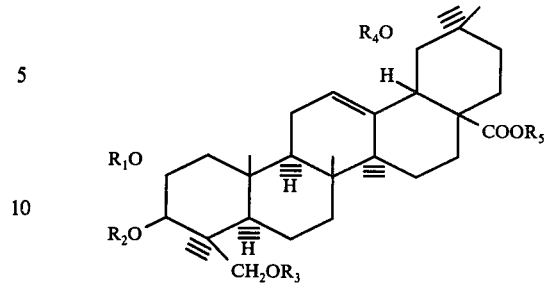

in which the hydrogen atom attached to $C_{18}$ is in the beta configuration, and in which $R_1$, $R_2$, $R_3$ and $R_4$ each represents a hydrogen atom or a substituted or unsubstituted aliphatic or aromatic mono-or polycarboxylic acid acyl radical, wherein when more than one of $R_1$, $R_2$, $R_3$ and $R_4$ are acyl radicals, they are the same acyl radical, and $R_5$ represents a hydrogen atom or a substituted or an unsubstituted aliphatic radical, and a pharmaceutically acceptable excipient.

28. A composition in accordance with claim 27, wherein the active principle is sericic acid.

29. A composition in accordance with claim 27, wherein the active principle is a dialkylaminoalkyl sericate.

30. A method of ellicting an anti-inflammatory effect in an animal, which comprises administering an anti-inflammatory amount of a compound as defined in claim 1.

31. A method of elliciting an anti-inflammatory effect in an animal, which comprises administering an anti-inflammatory amount of a compound as defined in claim 24.

32. A method of elliciting an anti-inflammatory effect in an animal, which comprises administering an anti-inflammatory amount of a composition in accordance with claim 27.

33. A method of elliciting an anti-inflammatory effect in an animal, which comprises administering an anti-inflammatory amount of a compound as defined in claim 28.

34. A method of elliciting an anti-inflammatory effect in an animal, which comprises administering an anti-inflammatory amount of a compound as defined in claim 29.

35. A pharmaceutical composition consisting essentially of a cicatrizing amount of an active principle of the general formula in which the hydrogen atom attached to $C_{18}$ is in the beta configuration, and in which $R_1$, $R_2$, $R_3$ and $R_4$ each represents a hydrogen atom or a substituted or unsubstituted aliphatic or aromatic mono/or polycarboxylic acid acyl radical, wherein when more than one of $R_1$, $R_2$, $R_3$ and $R_4$ are acyl radicals, they are the same acyl radical, and $R_5$ represents a hydrogen atom or a substituted or an unsubstituted aliphatic radical, and a pharmaceutically acceptable excipient.

36. A composition in accordance with claim 35, wherein the active principle is sericic acid.

37. A composition in accordance with claim 35, wherein the active principle is a dialkylaminoalkyl sericate.

38. A method of elliciting a cicatrizing effect in an animal, which comprises administering a cicatrizing amount of a compound as defined in claim 1.

39. A method of elliciting a cicatrizing effect in an animal, which comprises administering a cicatrizing amount of a compound as defined in claim 24.

40. A method of elliciting a cicatrizing effect in an animal, which comprises administering a cicatrizing amount of a composition in accordance with claim 35.

41. A method of elliciting a cicatrizing effect in an animal, which comprising administering a cicatrizing amount of a compound as defined in claim 36.

42. A method of elliciting a cicatrizing effect in an animal, which comprises administering a cicatrizing amount of a compound as defined in claim 37.

43. A pharmaceutical composition consisting essentially of an anti-inflammatory amount of the compound of claim 26 and a pharmaceutically acceptable excipient.

44. A method of elliciting an anti-inflammatory effect in an animal, which comprises administering an anti-inflammatory amount of a compound as defined in claim 26.

45. A pharmaceutical composition consisting essentially of a cicatrizing amount of the compound of claim 26 and a pharmaceutically acceptable excipient.

46. A method of elliciting a cicatrizing effect in an animal, which comprises administering a cicatrizing amount of a compound as defined in claim 26.

* * * * *